(12) United States Patent
Deng et al.

(10) Patent No.: US 11,814,649 B2
(45) Date of Patent: Nov. 14, 2023

(54) LITHIUM DISILICATE GLASS-CERAMIC COMPOSITIONS AND METHODS THEREOF

(71) Applicant: Corning Incorporated, Corning, NY (US)

(72) Inventors: Huayun Deng, Painted Post, NY (US);
Qiang Fu, Painted Post, NY (US);
John Christopher Mauro, Boalsburg, PA (US)

(73) Assignee: CORNING INCORPORATED, Corning, NY (US)

( * ) Notice: Subject to any disclaimer, the term of this patent is extended or adjusted under 35 U.S.C. 154(b) by 598 days.

(21) Appl. No.: 16/163,013

(22) Filed: Oct. 17, 2018

(65) Prior Publication Data
US 2019/0048318 A1  Feb. 14, 2019

Related U.S. Application Data

(62) Division of application No. 15/603,006, filed on May 23, 2017, now abandoned.
(Continued)

(51) Int. Cl.
| C03C 10/00 | (2006.01) |
| C03C 3/118 | (2006.01) |
| C03C 3/11  | (2006.01) |
| C03C 3/097 | (2006.01) |
| A61K 35/32 | (2015.01) |
| C03C 4/00  | (2006.01) |
| C12N 5/077 | (2010.01) |

(52) U.S. Cl.
CPC ............ *C12N 5/0654* (2013.01); *A61K 35/32* (2013.01); *C03C 3/097* (2013.01); *C03C 3/111* (2013.01); *C03C 3/118* (2013.01); *C03C 4/0014* (2013.01); *C03C 10/0009* (2013.01); *C03C 10/0027* (2013.01); *C03C 2204/00* (2013.01); *C03C 2205/06* (2013.01); *C12N 2533/12* (2013.01)

(58) Field of Classification Search
CPC .. C12N 5/0654; C12N 2533/12; A61K 35/32; C03C 4/0014; C03C 10/0009; C03C 3/097; C03C 3/111; C03C 3/118; C03C 10/0027; C03C 2204/00; C03C 2205/06; C03C 3/087
See application file for complete search history.

(56) References Cited

U.S. PATENT DOCUMENTS

| D219,017 S | 8/1879 | Rakes |
| 2,532,386 A | 12/1950 | Armistead |
(Continued)

FOREIGN PATENT DOCUMENTS

| CA | 2577628 C | 11/2010 |
| CA | 2926665 A1 | 5/2015 |
(Continued)

OTHER PUBLICATIONS

Liu et al. "The Effect of Novel Fluorapatite Surfaces on Osteoblast-Like Cell Adhesion, Growth, and Mineralization" Tissue Engineering: Part A, vol. 16, No. 9, 2010 (Year: 2010).*
(Continued)

*Primary Examiner* — Marcia S Noble
*Assistant Examiner* — Lauren K Van Buren (57) ABSTRACT

A bioactive glass-ceramic composition as defined herein. Also disclosed are methods of making and using the disclosed compositions.

14 Claims, 5 Drawing Sheets

Related U.S. Application Data (60) Provisional application No. 62/342,381, filed on May 27, 2016.

(56) References Cited

U.S. PATENT DOCUMENTS

| | | |
|---|---|---|
| 2,978,339 A | 4/1961 | Veatch et al. |
| 2,987,339 A | 6/1961 | Kaplan et al. |
| 3,323,888 A | 6/1967 | Searight et al. |
| 3,778,335 A | 12/1973 | Boyd |
| 3,790,430 A | 2/1974 | Mochel |
| 4,083,727 A | 4/1978 | Andrus et al. |
| 4,084,972 A | 4/1978 | Andrus et al. |
| 4,126,437 A | 11/1978 | O Horo |
| 4,140,645 A | 2/1979 | Beall et al. |
| 4,233,169 A | 11/1980 | Beall et al. |
| 4,323,056 A | 4/1982 | Borrelli et al. |
| 4,340,693 A | 7/1982 | Drake |
| 4,391,646 A | 7/1983 | Howell |
| 4,889,707 A | 12/1989 | Day |
| 5,024,973 A | 6/1991 | Kondo et al. |
| 5,081,394 A | 1/1992 | Morishita et al. |
| 5,153,070 A | 10/1992 | Andrus |
| 5,217,928 A | 6/1993 | Goetz et al. |
| 5,252,523 A | 10/1993 | Beall et al. |
| 5,648,124 A | 7/1997 | Sutor |
| 5,674,790 A | 10/1997 | Araujo |
| 5,849,816 A | 12/1998 | Suskind et al. |
| 5,876,452 A | 3/1999 | Athanasiou et al. |
| 6,034,014 A | 3/2000 | Rapp et al. |
| 6,214,471 B1 | 4/2001 | Beall |
| 6,254,981 B1 | 7/2001 | Castle |
| 6,280,863 B1 | 8/2001 | Frank et al. |
| 6,328,990 B1 | 12/2001 | Ducheyne et al. |
| 6,338,751 B1 | 1/2002 | Litkowski et al. |
| 6,506,399 B2 | 1/2003 | Donovan |
| 6,514,892 B1 | 2/2003 | Kasai et al. |
| 6,802,894 B2 | 10/2004 | Brodkin |
| 6,838,171 B2 | 1/2005 | Nomura |
| 6,852,656 B1 | 2/2005 | La Greca et al. |
| 7,047,634 B2 | 5/2006 | Nakamura |
| 7,047,637 B2 | 5/2006 | Derochemont et al. |
| 7,166,548 B2 | 1/2007 | Apel et al. |
| 7,166,549 B2 | 1/2007 | Fechner et al. |
| 7,192,602 B2 | 3/2007 | Fechner et al. |
| 7,316,740 B2 | 1/2008 | Schweiger et al. |
| 7,597,900 B2 | 10/2009 | Zimmer et al. |
| 7,704,903 B2 | 4/2010 | Seneschal et al. |
| 7,709,027 B2 | 5/2010 | Fechner et al. |
| 7,905,115 B2 | 3/2011 | Rake et al. |
| 7,914,874 B2 | 3/2011 | Henry et al. |
| 7,989,065 B2 | 8/2011 | Winstead |
| 8,080,490 B2 | 12/2011 | Fechner et al. |
| 8,173,154 B2 | 5/2012 | Jung et al. |
| 8,637,300 B2 | 1/2014 | Ruf et al. |
| 9,056,045 B2 | 6/2015 | Hughes |
| 9,084,844 B2 | 7/2015 | Vallittu |
| 9,101,439 B2 | 8/2015 | Ritzberger et al. |
| 9,168,272 B2 | 10/2015 | Hill et al. |
| 9,232,989 B2 | 1/2016 | Ritzberger et al. |
| 9,238,044 B2 | 1/2016 | Da et al. |
| 9,241,879 B2 | 1/2016 | Castillo |
| 9,326,995 B2 | 5/2016 | Stucky et al. |
| 9,371,249 B2 | 6/2016 | Ritzberger et al. |
| 9,498,459 B2 | 11/2016 | Pomrink et al. |
| 9,622,483 B2 | 4/2017 | Bookbinder et al. |
| 9,688,567 B2 | 6/2017 | Rampf et al. |
| 9,700,391 B2 | 7/2017 | Kounga et al. |
| 9,701,573 B2 | 7/2017 | Beall et al. |
| 2004/0120908 A1 | 6/2004 | Cohen et al. |
| 2004/0166172 A1 | 8/2004 | Rosati et al. |
| 2004/0228905 A1 | 11/2004 | Greenspan et al. |
| 2005/0118236 A1 | 6/2005 | Qiu et al. |
| 2005/0142077 A1 | 6/2005 | Zimmer et al. |
| 2005/0158395 A1 | 7/2005 | Zimmermann et al. |
| 2006/0127427 A1 | 6/2006 | Vernice et al. |
| 2006/0292280 A1 | 12/2006 | Soper et al. |
| 2007/0122356 A1 | 5/2007 | Kessler et al. |
| 2007/0281033 A1 | 12/2007 | Rochat |
| 2008/0214428 A1 | 9/2008 | Orlich et al. |
| 2008/0233201 A1 | 9/2008 | Royere |
| 2009/0208428 A1 | 8/2009 | Hill |
| 2009/0258778 A1 | 10/2009 | Castillo |
| 2009/0324668 A1 | 12/2009 | Kangasniemi et al. |
| 2011/0008293 A1 | 1/2011 | Bhandari |
| 2011/0009254 A1 | 1/2011 | Schweiger et al. |
| 2011/0152057 A1 | 6/2011 | Qi |
| 2012/0020898 A1 | 1/2012 | Mandadi et al. |
| 2012/0065756 A1* | 3/2012 | Rubbert ............. A61L 27/3865 700/98 |
| 2012/0135848 A1 | 5/2012 | Beall et al. |
| 2012/0317735 A1 | 12/2012 | Gonzales |
| 2012/0321567 A1 | 12/2012 | Gonzales |
| 2013/0011446 A1 | 1/2013 | Depaula |
| 2013/0266625 A1 | 10/2013 | Benita |
| 2014/0000891 A1 | 1/2014 | Mahoney et al. |
| 2014/0026916 A1 | 1/2014 | Havens |
| 2014/0135202 A1 | 5/2014 | Ritzberger et al. |
| 2014/0186274 A1 | 7/2014 | Hodgkinson |
| 2014/0193499 A1* | 7/2014 | Da Fonte Ferreira . A61K 33/00 424/692 |
| 2014/0212469 A1 | 7/2014 | Rahaman |
| 2014/0028196 A1 | 8/2014 | Ritzberger et al. |
| 2014/0219941 A1 | 8/2014 | Takekawa et al. |
| 2014/0271913 A1 | 9/2014 | Pomrink et al. |
| 2014/0349831 A1 | 11/2014 | Cornejo et al. |
| 2014/0370464 A1 | 12/2014 | Kounga et al. |
| 2015/0087493 A1 | 3/2015 | Ritzberger |
| 2015/0104655 A1 | 4/2015 | Kim et al. |
| 2015/0231042 A1 | 8/2015 | Gonzales |
| 2015/0239772 A1 | 8/2015 | Baker |
| 2015/0265509 A1 | 9/2015 | Zhang et al. |
| 2015/0274581 A1 | 10/2015 | Beall et al. |
| 2015/0299031 A1 | 10/2015 | Ritzberger et al. |
| 2015/0374589 A1 | 12/2015 | Rampf et al. |
| 2016/0060159 A1* | 3/2016 | Kim ................. A61C 13/0006 501/63 |
| 2016/0102010 A1 | 4/2016 | Beall et al. |
| 2016/0145567 A1 | 5/2016 | Henry et al. |
| 2016/0340239 A1 | 11/2016 | Propster et al. |
| 2017/0086877 A1 | 3/2017 | Moffarah et al. |
| 2017/0274118 A1 | 9/2017 | Nazhat et al. |
| 2017/0340527 A1 | 11/2017 | Chang et al. |
| 2017/0340666 A1 | 11/2017 | Deng et al. |
| 2017/0341975 A1 | 11/2017 | Gross et al. |
| 2017/0342382 A1 | 11/2017 | Deng et al. |
| 2017/0342383 A1 | 11/2017 | Deng et al. |
| 2017/0349876 A1 | 11/2017 | Deng et al. |
| 2017/0354755 A1 | 12/2017 | Weinberger et al. |
| 2018/0343255 A1 | 11/2018 | Thibadeau, Sr. et al. |
| 2019/0060523 A1 | 2/2019 | Bakry |

FOREIGN PATENT DOCUMENTS

| | | |
|---|---|---|
| CN | 1032265 A | 4/1989 |
| CN | 1054055 A | 8/1991 |
| CN | 1155844 A | 7/1997 |
| CN | 1213355 A | 4/1999 |
| CN | 1325291 A | 12/2001 |
| CN | 1615280 A | 5/2005 |
| CN | 1838936 A | 9/2006 |
| CN | 101018573 A | 8/2007 |
| CN | 101407373 A | 4/2009 |
| CN | 101500622 A | 8/2009 |
| CN | 101596326 A | 12/2009 |
| CN | 101704632 A | 5/2010 |
| CN | 101808955 A | 8/2010 |
| CN | 101938877 A | 1/2011 |
| CN | 102421716 A | 4/2012 |
| CN | 102430149 A | 5/2012 |
| CN | 102526797 A | 7/2012 |
| CN | 103172263 A | 6/2013 |
| CN | 103449725 A | 12/2013 |
| CN | 103930086 A | 7/2014 |
| CN | 103979796 A | 8/2014 |

(56) References Cited

FOREIGN PATENT DOCUMENTS

| | | |
|---|---|---|
| CN | 104039729 A | 9/2014 |
| CN | 104108883 A | 10/2014 |
| CN | 104379113 A | 2/2015 |
| CN | 104736126 A | 6/2015 |
| CN | 104876439 A | 9/2015 |
| CN | 105236745 A | 1/2016 |
| CN | 105819697 A | 8/2016 |
| CN | 107028770 A | 8/2017 |
| DE | 10214273 A1 | 10/2003 |
| DE | 102005026269 A1 | 12/2006 |
| EP | 0583791 A1 | 2/1994 |
| EP | 0885855 A2 | 12/1998 |
| EP | 935526 A1 | 8/1999 |
| EP | 1116698 A1 | 7/2001 |
| EP | 1123072 A1 | 8/2001 |
| EP | 1233721 A1 | 8/2002 |
| EP | 1452496 A1 | 9/2004 |
| EP | 1580172 A2 | 9/2005 |
| EP | 1021148 B1 | 5/2008 |
| EP | 2868634 A1 | 5/2015 |
| EP | 2868634 A1 * 5/2015 ............ A61K 6/024 | |
| EP | 3095436 A1 | 11/2016 |
| HU | 0302501 A2 | 1/2006 |
| HU | 227595 B1 | 9/2011 |
| JP | 2001-010843 A | 1/2001 |
| JP | 3306811 B2 | 7/2002 |
| JP | 2004359754 A | 12/2004 |
| JP | 2005-053776 A | 3/2005 |
| JP | 2005-255517 A | 9/2005 |
| JP | 2007001846 A | 1/2007 |
| JP | 2007039269 A | 2/2007 |
| JP | 2015-504399 A | 2/2015 |
| JP | 2015-505786 A | 2/2015 |
| JP | 2015-509016 A | 3/2015 |
| JP | 2015-525180 A | 9/2015 |
| KR | 200781952 | 8/2007 |
| KR | 10-0781952 B1 | 12/2007 |
| KR | 10-2013-0112422 A | 10/2013 |
| KR | 20130112433 A | 10/2013 |
| WO | 87/07256 A1 | 12/1987 |
| WO | 1991012032 A1 | 8/1991 |
| WO | 1997018171 A1 | 5/1997 |
| WO | 9727148 A1 | 7/1997 |
| WO | 97/27884 A1 | 8/1997 |
| WO | 98/08672 A1 | 3/1998 |
| WO | 1998015263 A2 | 4/1998 |
| WO | 1999062835 A1 | 12/1999 |
| WO | 00/15167 A1 | 3/2000 |
| WO | 01/34060 A1 | 5/2001 |
| WO | 2006/072394 A1 | 7/2006 |
| WO | 2007/022264 A2 | 2/2007 |
| WO | 2007141978 A1 | 12/2007 |
| WO | 2008000888 A2 | 1/2008 |
| WO | 2011/084572 A2 | 7/2011 |
| WO | 2011141896 A1 | 11/2011 |
| WO | 2012/091201 A1 | 7/2012 |
| WO | 2012137158 | 10/2012 |
| WO | 2014/015240 A1 | 1/2014 |
| WO | 2014/052973 A1 | 4/2014 |
| WO | 2014095198 A1 | 6/2014 |
| WO | 2014159240 A1 | 10/2014 |
| WO | 2015034860 | 3/2015 |
| WO | 2015123049 A1 | 8/2015 |
| WO | 2015200017 A1 | 12/2015 |
| WO | 2017/205589 A1 | 11/2017 |

OTHER PUBLICATIONS

Ning et al. "Effects of silica on the bioactivity of calcium phosphate composites in vitro" Journal of Materials Science: Materials in Medicine 16 (2005) 355-360 (Year: 2005).*
Gorustovich et al. "Osteoconductivity of strontium-doped bioactive glass particles: A histomorphometric study in rats," J Biomed Materials Res. Part A (2010) 92A: pp. 232-237.
Harianawala et al. "Biocompatibility of Zirconia", J Adv Med Deni Sci Res 4(3) 2016, pp. 35-39.
International Search Report and Written Opinion PCT/US2017/034421 dated Jul. 21, 2017.
Mohini et al; "Studies on Influence of Aluminium Ions on the Bioactivity of $B_2O_3$—$SiO_2$—$P_2O_5$—$Na_2O$—CaO Glass System by Means of Spectroscopic Studies" ; Applied Surface Science; 287 (2013) pp. 46-53.
Noris-Suarez et al; "Osteoblastic Cells Biomineralized on Bioactive Glass and Glass-Ceramics of the $SiO_2Na_2O.CaO.K_2O.MgO.P_2O_5$ System Modified With $Al_2O_3$ and $B_2O_3$"; Journal of Ceramic Processing Research; vol. 11, No. 2 (2010) pp. 129-137.
Pires et al; "The Role of Alumina in Aluminoborosilicate Glasses for Use in Glass-Ionomer Cements" ; J. Mater. Chem, 19 (2009) pp. 3652-3660.
International Search Report and Written Opinion of the International Searching Authority; PCT/US17/034421; dated July 20, 2017; 12 pages; European Patent Office.
"An In-Vitro Comparison of Nano Hydroxyapatite, Novamin and Proargin Desensitizing Toothpastes—A SEM Study"; J Clin Diagn Res, 2016, 10(10): ZC51ZC54.
Bertling, et al., "Hollow Microspheres" . Chem Eng Technol, 2004, 27: 829-837.
Budov, "Hollow Glass Microspheres. Use, Properties and Technology (Review Article)", Glass Ceram, 1994, 51: 230-235.
Cao et la; "Methods for Biomimetic Remineralization of Human Dentine: A Systematic Review" ; Int. J. Mol. Sci. (2015) 16; pp. 4615-4627.
Copeland et al.; "Microbeads: An Emerging Water Quality Issue", Retrieved From fas.org, Jul. 20, 2015, 2 Pgs.
Coradin et al; "Silica-Alginate Composites for Microencapsulation" Applied Microbiology and Biotechnology, 61(5-6) pp. 429-434 (2003.
Davari, "Dentin Hypersensitivity: Etiology, Diagnosis and Treatment, A Literature Review," J Dent (Shiraz), 2013, 14(3): 136145).
Strassler et al; Dentinal Hypersensitivity: Etiology, Diagnosis and Management "; 9 Pages; Date Unknown; www.indeedce.com".
El-Kheshen et al. Ceramics Int. (2008) 34: 1667-1673 (Year: 2008).
Fendall et al; "Contributing to Marine Pollution by Washing Your Face: Microplasitcs in Facial Cleansers" ; Marine Pollution Bulletin 58 (8): 12251228 (2009.
Forsback et al; "Mineralization of Dentin Induced by Treatment With Bioactive Glass S53P4 in Vitro" ; Acta Odontol Scand, 62 (2004); pp. 14-20.
Fu et al.; "Bioactive Glass Innovations Through Academia-Industry Collaboration" ; International Journal of Applied Glass Science, 7 [2], (2016) pp. 139-146.
Fu et al; "Hollow Hydroxyapatite Microspheres as a Device for Controlled Delivery of Proteins" ; J Mater Sci: Mater Med., 2011;22:579-91.
Fu et al.; "Nature-Inspired Design of Strong, Tough Glass-Ceramics," MRS Bulletin, 2017, 42:220-225.
Graham, "High-Sensitivity Manetization Measurements" , J. Mater. Sci. Technol., vol. 16, No. 2, 2000, p. 97-101.
Gy, "Ion Exchange for Glass Strengthening," Mater Sci Ehg B, 2008, 149: 159-165.
Han et al.; "In Vivo Remineralization of Dentin Using an Agarose Hydrogel Biomimetic Mineralization System" ; Nature, Scientific Reports; (2017); 9 PAGES.
Holand et al; "A Comparison of the Microstructure and Properties of the IPS EMPRESST2 and the IPS EMPRESST Glass-Ceramics" ; J Biomed Mater Res (Appl Biomater) , 2000, 53: 297303.
Huang et al.; "Kinetics and Mechanisms of the Conversion of Silicate (45S5), Borate and Borosilicate Glasses to Hydroxyapatite in Dilute Phosphate Solutions," J Mater Sci Mater Med 2006, 17: 583-596.
Jacoby; "New Applications for Glass Emerge," Chem. Eng. News, 90 [25] 3436 (2012).
Jones; "Review of Bioactive Glass: From Hench to Hybrids" ; Acta Biomaterialia 9 (2013) pp. 4457-4486.

(56) References Cited

OTHER PUBLICATIONS

Kulal et al; "An In-Vitro Comparison of Nano Hydroxyapatite, Novamin and Proargin Desensitizing Toothpastes—A Sem Study" ; Journal of Clinical and Diagnostic Research; 2016; vol. 10 (10) ZC51-ZC54.

Kumaryadav et al; "Development of Zirconia Substituted 1393 Bioactive Glass for Orthopaedic Application" ; Oriental Journal of Chemistry; vol. 33, No. 6; (2017) pp. 2720-2730.

Lien et al.; "Microstructural Evolution and Physical Behavior of a Lithium Disilicate Glass- Ceramic" ; Dent Mater 2015, 31: 928-940.

Low et al.; "Reduction in Dental Hypersensitivity With Nano-Hydroxyapatite, Potassium Nitrate, Sodium Monoflurophosphate and Antioxidants" ; The Open Dentistry Journal; (2015), 9, pp. 92-97.

Marcolongo et al; "Surface Reaction Layer Formation In Vitro on a Bioactive Glass Fiber/Polymeric Composite" ; J. Biomed Mater. Res.; (1997); 37, pp. 440-448.

Miglani et al; "Dentin Hypersensitivity: Recent Trends in Management" ; J. Conserv. Dent. 2010; 13 (4) pp. 218-224.

Mintatoya et al; "Bioactive Glass Cloth That Propmotes New Bone Formation" ; Key Eng. Mater.; (2013) 529-530; pp. 266-269.

Ohgushi et al; Bioceramics vol. 11, Legeros et al, Ed., Proc. 11th Int. Symp. Ceramics. Med. (NY:NY), Nov. 1998, pp. 261-264 (Year 1998).

Ramanujan, Book Chapter 17, Magnetic Particles for Biomedical Applications, R. Narayan (ed.), Biomedical Materials, DOI 10.1007/978-0-387-84872-3 17, C Springer Science+Business Media, LLC 2009, pp. 477-491.

Sglavo; "Chemical Strengthening of Soda Lime Silicate Float Glass: Effect of Small Differences in the KNO3 Bath," Int J Appl Glass Sci, 2015, 6: 72-82.

Simhan; "Chemical Durability of ZrO2 Containing Glasses" ; Journal of Non-Crystalline Solids; 54 (1983) 335-343.

Singh et al; "Characterization of SI02-NA20-FE203-CA0-P205_B203 Glass Ceramics" ; Journal of Materials Science: Materials in Medicine, 10(8) pp. 481-484. (1999).

Succaria et al; "Prescribing a Dental Ceramic Material: Zirconia vs Lithium-Disilicate" ; The Saudi Dent J, 2011, 23: 165-166.

Wallenberger et al; "The Liquidus Temperature; Its Critical Role in Glass Manufacturing"; International Journal of Applied Glass Science 1 [2] (2010) pp. 151-163.

Yao et al; "In Virto Bioactive Characteristics of Borate-Based Glasses With Controllable Degradation Behavior" ; J. Am. Ceram. Soc.; 90 [1]; 303-306 (2007).

Yin et al; "Effect of ZrO2 on the Bioactivity Properties of Gel-Derived CaO—P2O5—SiO2—SrO Glasses" ; Ceramics International; 43 (2017) pp. 9691-9698.

Yue et al; "Fiber Spinnability of Glass Melts" ; International Journal of Applied Glass Science; (2016) pp. 1-11.

Zhang et al; "Chipping Resistance of Graded Zirconia Ceramics for Dental Crowns" ; J Dent Res, 2012, 91:311315.

Fu etal. J. Biomed. Res. (2010) 95A(1): 164-171(Year:2010).

Abo-Naf et al; "In Vitro Bioactivty Evaluation, Mechnical Properties and MicroStructural Characterization of Na2O—CaO—B2O3—P2O5 glasses"; Spectrochimica Acta Part A: Molecular and Biolmoleclar Spectroscopy; 144 (2015) pp. 88-98.

Sharmikn et al; "Effect of Boron Additiona on the Thermal, Degradation, and Cytocompatibility Properties of Phosphate-based Glasses"; Biomed Research International; vol. 2013; Article ID 902427; 12 Pages.

Buchilin et al; "Crystallization-Controlled Pore Retention in Calcium-Phosphate Glassceramics From Powder Sintering of CaO—P2O5—B2O3—Al2O3—TiO2—ZrO2 Glass"; Journal of Non-Crystalline Solids; 373-374 (2013) pp. 42-50.

Zheng et al; "Characteristics and Biocompatibility of Na2O—K2O—CaO—MgO—SrO—B2O3—P2O5 Borophosphate Glass Fibers"; Journal of Non-Crystalline Solid; 358 (2012) 287-391.

Azo Materials, ""Silicon Dioxide"", accessed from: ""https://www.azom.com/properties.aspx?ArticleI D=1114"", accessed on Feb. 19, 2019,pp. 1-4 (Year: 2019).

Kaklamani et al; "Mechanical Properties of Alginate Hydrogels Manufactured Using External Gelation", J. Meech Beh. Biomed. Mater., 2014, pp. 135-142 (Year:2014.

Maestrelli et al; "Development of Enteric-Coated Calcium Pectinate Microspheres Intended for Colonic Drug Delivery", Eur. J. Pharm. and Biopharm., 2008, pp. 508-518 (Year: 2008).

Japanese Patent Application No. 2018561573 Office Action dated Febuary 24, 2021, 14 pages (7 pages of English Translation and 7 pages of Original Document); Japanese Patent Office.

Zahid et al; "Biological Behavior of Bioactive Glasses and Their Composites" ; RSC Adv., 2016, 6 pp. 70197 - 70214.

Graham; "High-Sensitivity Magnetization Measurements"; J. Mater. Sci. Technol., vol. 16, No. 2 (2000) pp. 97-101.

L. Hench et al., "Third-Generation Biomedical Materials", Science, vol. 295, Feb. 8, 2002, pp. 1016-1017, www.sciencemag.org, Downloaded from www.sciencemag.org on Aug. 5, 2015.

L.L.Hench, "Bioceramics", J. Am. Ceram. Soc., 81, (7), 1705-1728 (1998).

T. Kokubo et al., "How useful is SBF in predicting in vivo bone bioactivity?", Biomaterials, 27, (2006), 2907-2915.

Qiang Fu et al., "Bioactive glass scaffolds for bone tissue engineering: state of the art and future perspectives", Materials Science and Engineering, C 31, (2011), 1245-1256.

L. Peddi et al., "Bioactive borate glass coatings for titanium alloys", J. Mater. Sci: Mater. Med., (2008), 19, p. 3145-3152.

Mohamed N. Rahaman et al., "Bioactive glass in tissue engineering", Acta Biomaterialia, 7, (2011), 2355-2373.

WO2012137158 machine translation.

Dutra Zanotto, "A bright future for glass-ceramics", American Ceramic Society Bulletin, vol. 89, No. 8, pp. 19-27.

American Type Culture Collection, Product Sheet MC3T3E1, Subclone 14, (ATCC® CRL2594™), p. 1-3, Aug. 2014.

Maziar Montazerian, et al. "History and trends of bioactive glass-ceramics", Journal of Biomedical Materials Research A, 2016, vol. 104A, 1231-1249, 2016 Wiley Periodicals, Inc.

Apel et al., "Influence of ZrO2 on the crystallization and properties of lithium disilicate glass-ceramics derived from a multi-component system", J Eur Ceram Soc, 2007, 27:1571-1577.

Antonio Tilocca et al., "Structural Effects of Phosphorus Inclusion in Bioactive Silicate Glasses", J. Phys. Chem. B 2007, 111, 14256-14264.

K. Franks et al., "The effect of MgO on the solubility behaviour and cell proliferation in a quaternary soluble phosphate baed glass system", J. of Mate. Sciemce: Materials in Medicine, 13, (2002), 549-556.

I. Ahmed et al., "Processing, characterisation and biocompatibility of iron-phosphate glass fibres for tissue engineering", Biomaterials, 25, (2004), 3223-3232.

Huipin Yuan, et al., "Osteoinduction by calciumphosphate biomaterials", Journal of Materials Science: Materials in Medicine 9 (1998) 723-726.

Jianxi Lu, et al., The Biodegradation Mechanism of Calcium Phosphate Biomaterials in Bone, Journal of Biomedical Materials Research, Aug. 2002, 63(4): 408-412.

B.C. Bunker, et al., Phosphate Glass Dissolution in Aqueous Solutions, Journal of Non-Crystalline Solids 64 (1984) 291-316.

Jonathan C. Knowles, Phosphate based glasses for biomedical applications, J. Mater. Chem., 2003, 13, 2395-2401.

Motohiro Uo et al., Properties and cytotoxicity of water soluble Na2O—CaO—P2O5 glasses, Biomaterials, 19, (1998), 2277-2284.

F. Jay Murray, Issues in Boron Risk Assessment: Pivotal Study, Uncertainty Factors, and ADIs, The Journal of Trace Elements in Experimental Medicine 9, No. 4 (1996): 231-243.

R.F. Brown, et al., "Effect of borate glass composition on its conversion to hydroxyapatite and on the proliferation of MC3T3-E1 cells." Journal of Biomedical Materials Research Part A, 88, No. 2, (2009): 392-400.

A. Saranti, et al., "Bioactive glasses in the system CaO—B2O3—P2O5: preparation, structural study and in vitro evaluation." Journal of Non-Crystalline Solids 352, No. 5 (2006): 390-398.

L. Hench, and J. Jones, eds. Biomaterials, artificial organs and tissue engineering. Elsevier, 2005—book.

(56) References Cited

OTHER PUBLICATIONS

E.A. Abou Neel, et al., "Effect of iron on the surface, degradation and ion release properties of phosphate-based glass fibres." Acta Biomaterialia 1, No. 5 (2005): 553-563.
E.A. Abou Neel, et al., "Characterisation of antibacterial copper releasing degradable phosphate glass fibres.", Biomaterials 26, No. 15 (2005): 2247-2254.
C. M. Rochman, et al., Scientific evidence supports a ban on microbeads, Environ Sci & Tech, 2015, 49: 10759-10761.
Wei Xiao et al., "Hollow hydroxyapatite microspheres: a novel bioactive and osteoconductive carrier for controlled release of bone morphogenetic protein-2 in bone regeneration", Acta Biomater. Sep. 2013 ; 9(9): 8374-8383.
Wanpeng Cao et al., Bioactive Materials, Ceramics International, 22, (1996) 493-507.
Fabienne C. Raszewski et al., Methods for Producing Hollow Glass Microspheres, Savannah River National Laboratory, Aiken, SC 29808, Mar. 2016.
Imogen E. Napper et al., Characterisation, quantity and sorptive properties of microplastics extracted from cosmetics, Marine Pollution Bulletin, vol. 99, Issues 1-2, Oct. 15, 2015, pp. 178-185.
Alexis J. de Kerchove et al., Formation of Polysaccharide Gel Layers in the Presence of Ca2+ and K+ Ions: Measurements and Mechanism, Biomacromolecules, 2007, 8, 113-121.
Marianne Hiorth et al., Immersion coating of pellets with calcium pectinate and chitosan, International Journal of Pharmaceutics 308 (2006) 25-32.
Fuat Topuz, et al., Magnesium ions and alginate do form hydrogels: a rheological study, Soft Matter, 2012, 8, 4877-4881.
Yrr A. Mørch, et al., Effect of Ca2+, Ba2+, and Sr2+ on Alginate Microbeads, Biomacromolecules 2006, 7, 1471-1480.
Andersson et al. "In vivo behaviour of glasses in the SiO2—Na2O—CaO—P2O5—Al2O3—B2O3 system" , J. Mat. Sci: Materials in Medicine (1990) 1: pp. 219-227.
Gunter et al. "Calcium pectinate gel beads obtained from callus cultures pectins aspromising systems for colon-targeted drug delivery," Carbohydrate Polymers, 2016, pp. 490-499.
Ogonczyk et al. "Microfluidic formulation of pectin microbeads for encapsulation and controlled release of nanoparticles," Biomicrofluidics, 2011, pp. 1-12.
G. Jagan Mohini et, al., "Studies on influence of aluminium ions on the bioactivity of B2O3-Si02-P2O5-Na2O-CaO glass system by means of spectroscopic", Applied Surface Science, vol. 287, 2013, pp. 46-53.
Karem Noris-Suarez et, al., "Osteoblastic cells biomineralized on bioactive glass and glass-ceramics of the SiO2.Na2O.CaO.K 20.Mg O.P2O5 system modified with Al2O3 and B2O3", Journal of Ceramic Processing Research, vol. 11, No. 2, 2020, 9 pages.
Ricardo A. Pires et, al., "The role of alumina in aluminoborosilicate glasses for use in glass-inomercementa", Journal of Materials Chemistry, vol. 19, 2009, pp. 3652-3660.
Ning et al., "Food Biochemistry" South China University of Technology Press, Edition 1, 1995, 9 pages (5 pages of English Translation and 14 pages of Original Document).
Chinese Patent Application No. 201780032893, Office Action dated May 17, 2021; 14 pages (English Translation only); Chinese Patent Office.
Wang Yingjun, "Biomedical Ceramic Materials", Guangzhou, South China University of Science and Technology Press, , Aug. 31, 2010, pp. 90-93(Original document only).
Ohgushi et al., "Al2O3 doped apatite-wollastonite containing glass ceramic provokes osteogenic differentiation of marrow stromal stem cells", J Biomed Mater Re, vol. 44, Issue 4 pp. 381-388.
Zhao et al., "Mechanism for converting Al2O3-containing borate glass to hydroxyapatite in aqueous phosphate solution", Acta Biomaterialia, Dec. 10, 2008, vol. 5, No. 4, pp. 1265-1273.
Chinese Patent Application No. 201780032893.X, Office Action dated Nov. 17, 2021, 4 pages English Translation, Chinese Patent Office.

* cited by examiner

LITHIUM DISILICATE GLASS-CERAMIC COMPOSITIONS AND METHODS THEREOF

CROSS REFERENCE TO RELATED APPLICATIONS

This application is a divisional of U.S. Non-Provisional patent application Ser. No. 15/603,006, filed May 23, 2017 and entitled "LITHIUM DISILICATE GLASS-CERAMIC COMPOSITIONS AND METHODS THEREOF," which claims the benefit of priority under 35 U.S.C. § 119 of U.S. Provisional Patent Application No. 62/342,381 filed May 27, 2016, the contents of both of which are relied upon and incorporated herein by reference in their entirety.

CROSS-REFERENCE TO RELATED APPLICATIONS

The present application is related commonly owned and assigned USSN Provisional application Nos., filed concurrently herewith:
62/342,384, entitled "BIOACTIVE ALUMINOBORATE GLASSES";
62/342,377, entitled "MAGNETIZABLE GLASS CERAMIC COMPOSITION AND METHODS THEREOF";
62/342,391, entitled "BIODEGRADABLE MICROBEADS";
62/342,411, entitled "BIOACTIVE GLASS MICROSPHERES"; and
62/342,426, entitled "BIOACTIVE BOROPHOSPHATE GLASSES"; but does not claim priority thereto.

The present application is also related to commonly owned and assigned USSN Application No. 62/189,880, filed Jul. 7, 2015, entitled "ANTIMICROBIAL PHASE-SEPARATING GLASS AND GLASS CERAMIC ARTICLES AND LAMINATES," which mentions a copper containing laminate having a degradable phase, which phase liberates cooper ion, and a non-degradable phase; and 61/874,870, filed Sep. 6, 2013, entitled "High strength glass-ceramics having lithium disilicate and beta-spodumene structures," but does not claim priority thereto The entire disclosure of each publication or patent document mentioned herein is incorporated by reference.

BACKGROUND

The disclosure relates to glass-ceramic compositions, bioactive glass-ceramic compositions and articles made from the glass-ceramic compositions, and to methods of making and using the bioactive glass-ceramic compositions and articles.

SUMMARY

In embodiments, the disclosure provides a group of glass-ceramic compositions each having lithium disilicate as a first major crystal phase, and at least one of wollastonite, fluoroapatite, cristobalite, β-quartz, lithiophosphate, or a mixture thereof, as a second minor phase.

In embodiments, the disclosed compositions can comprise a source of, for example, 50 to 75 wt % $SiO_2$, 1 to 5 wt % $Al_2O_3$, 1 to 8 wt % $P_2O_5$, 2 to 10 wt % CaO, 5 to 20 wt % $Li_2O$, 0.5 to 5 wt % $Na_2O$, 0.5 to 8 wt % $ZrO_2$, and 0.1 to 1.0 $F^-$ wt % (i.e., fluoride ion), based on a 100 wt % total of the composition.

In embodiments, the disclosed compositions can further comprise a source of, for example, 0.1 to 10 wt % $B_2O_3$, based on a 100 wt % total of the composition.

In embodiments, the disclosure provides a glass-ceramic composition or glass-ceramic articles made from the composition, having a combination of high strength and high toughness.

In embodiments, the disclosure provides a glass-ceramic composition having excellent biocompatibility.

In embodiments, the disclosure provides methods of making and using the disclosed compositions.

BRIEF DESCRIPTION OF THE DRAWINGS

In embodiments of the disclosure.

DETAILED DESCRIPTION

Various embodiments of the disclosure will be described in detail with reference to drawings, if any. Reference to various embodiments does not limit the scope of the invention, which is limited only by the scope of the claims attached hereto. Additionally, any examples set forth in this specification are not limiting and merely set forth some of the many possible embodiments of the claimed invention.

In embodiments, the disclosed method of making and using provide one or more advantageous features or aspects, including for example as discussed below. Features or aspects recited in any of the claims are generally applicable to all facets of the invention. Any recited single or multiple feature or aspect in any one claim can be combined or permuted with any other recited feature or aspect in any other claim or claims.

Definitions

"Glass," "glasses," or like terms can refer to a glass or a glass-ceramic.

"Glass article," or like terms can refer to any object made wholly or partly of any of the disclosed glass or glass-ceramic compositions.

"Bioactivity Index" "index of bioactivity," "$I_B$," or like terms or symbols refer to, for example, the time for more than 50% of the interface of a specific bioactive material to be bonded by a biological material such as bone, tissue, and like materials. Mathematically, a bioactivity index (according to Hench; see Cao, W., et al., Bioactive Materials, Ceramics International, 22 (1996) 493-507) is, $I_B=100/t_{0.5bb}$, where $t_{0.5bb}$ is the time for more than 50% of a bioactive material's interface, such as an implant, to be bonded by a biological material such as bone, tissue, and like materials, including osteoproductive (Class A having both intracellular and extracellular responses, e.g., 45S5 Bioglass®) and osteoconductive (Class B extracellular response only at interface, e.g., synthetic hydroxyapatite) materials.

"Include," "includes," or like terms means encompassing but not limited to, that is, inclusive and not exclusive.

"About" modifying, for example, the quantity of an ingredient in a composition, concentrations, volumes, process temperature, process time, yields, flow rates, pressures, viscosities, and like values, and ranges thereof, or a dimension of a component, and like values, and ranges thereof, employed in describing the embodiments of the disclosure, refers to variation in the numerical quantity that can occur, for example: through typical measuring and handling procedures used for preparing materials, compositions, composites, concentrates, component parts, articles of manufacture, or use formulations; through inadvertent error in these procedures; through differences in the manufacture, source, or purity of starting materials or ingredients used to carry out the methods; and like considerations. The term "about" also encompasses amounts that differ due to aging of a composition or formulation with a particular initial concentration or mixture, and amounts that differ due to mixing or processing a composition or formulation with a particular initial concentration or mixture.

"Optional" or "optionally" means that the subsequently described event or circumstance can or cannot occur, and that the description includes instances where the event or circumstance occurs and instances where it does not.

The indefinite article "a" or "an" and its corresponding definite article "the" as used herein means at least one, or one or more, unless specified otherwise.

Abbreviations, which are well known to one of ordinary skill in the art, may be used (e.g., "h" or "hrs" for hour or hours, "g" or "gm" for gram(s), "mL" for milliliters, "rt" for room temperature, "nm" for nanometers, and like abbreviations).

Specific and preferred values disclosed for components, ingredients, additives, dimensions, conditions, times, and like aspects, and ranges thereof, are for illustration only; they do not exclude other defined values or other values within defined ranges. The composition and methods of the disclosure can include any value or any combination of the values, specific values, more specific values, and preferred values described herein, including explicit or implicit intermediate values and ranges.

Bioactive materials having high strength and toughness are in significant demand, for example, for the regeneration of bone and teeth. Glass-ceramics based on lithium disilicate offer highly desirable mechanical properties, including high body strength and fracture toughness, due to their microstructures of randomly-oriented interlocking crystals. Glass-ceramics having fracture toughness values of 2 to 3 MPa·m$^{1/2}$ are achievable in the system of glass-ceramics based on lithium disilicate compositions (see commonly owned and assigned U.S. Ser. No. 61/874,870). Lithium disilicate glass-ceramics have been widely used in the fabrication of single and multiple dental restorations. However, these glass-ceramics have not been used in bone repair due to their relatively low bioactivity. In contrast, bioceramics based on apatite and wollastonite have demonstrated high bioactivity but do not have sufficient mechanical strength compared to, for example, cortical bone (Hench, L. L., Bioceramics, *J Am Ceram Soc*, 1998, 81: 1705-1728).

In embodiments, the disclosure provides a group of glass-ceramic compositions having a phase assemblage containing a major phase of lithium disilicate and a minor phase or phases of, for example, apatite or wollastonite. These superior compositions exhibit an excellent combination of high mechanical strength and high bioactivity, which makes them excellent for hard tissue regeneration.

WO 2015200017 ('017), entitled "Process for producing a sintered lithium disilicate glass ceramic dental restoration and kit of parts," mentions a process for producing a sintered lithium disilicate glass ceramic dental restoration out of a porous 3-dim article. In contrast, the presently disclosed compositions have a different phase assemblage, for example, the disclosed compositions have lithium disilicate and apatite, whereas '017 has only lithium disilicate, and the presently disclosed compositions are bioactive but not the '017 compositions. Additionally, the presently disclosed compositions have CaO and F to produce the apatite phase.

US 20150087493 mentions lithium disilicate apatite glass-ceramics, which are characterized by a high chemical stability and can be used as restoration material in dentistry. However, these materials all include $K_2O$, which is absent from the presently disclosed compositions.

U.S. Pat. No. 7,166,548 mentions an apatite glass ceramic, which contains at least one glass phase and at least one apatite phase and is characterized in that at least one of the apatite phases is a phosphate-free and fluorine-free siliceous oxyapatite phase. However, these materials exclude phosphate and fluorine, which is present in the presently disclosed compositions.

In embodiments, the disclosure provides a glass-ceramic composition, comprising:
  a first crystalline phase comprised of lithium disilicate; and
  a second crystalline phase selected from the group consisting of at least one of: wollastonite, fluoroapatite, cristobalite, β-quartz, lithiophosphate, or a combination thereof.

In embodiments, the disclosure provides a glass-ceramic composition wherein the first crystalline phase and the second crystalline phase, in combination, comprise a source of:
  50 to 75 wt % $SiO_2$,
  1 to 5 wt % $Al_2O_3$,
  1 to 8 wt % $P_2O_5$,
  2 to 10 wt % CaO,
  5 to 20 wt % $Li_2O$,
  0.5 to 5 wt % $Na_2O$,
  0.5 to 8 wt % $ZrO_2$, and
  0.1 to 1.0 wt % $F^-$, i.e., fluoride ion, based on a 100 wt % total of the composition.

In embodiments, the glass-ceramic composition can further comprise a source of 0.1 to 10 wt % $B_2O_3$, based on a 100 wt % total of the composition.

In embodiments, the first crystalline phase and the second crystalline phase, in combination, can comprise a source of:
  50 to 60 wt % $SiO_2$,
  1 to 3 wt % $Al_2O_3$,
  2 to 6 wt % $P_2O_5$,
  4 to 8 wt % CaO.
  7.5 to 12.5 wt % $Li_2O$,
  0.5 to 2 wt % $Na_2O$,
  1 to 4 wt % $ZrO_2$, and
  0.2 to 0.8 wt % $F^-$, based on a 100 wt % total of the composition.

In embodiments, the abovementioned composition can be a preferred or a most preferred composition and can comprise, consist of, or consist essentially of, the abovementioned composition components.

In embodiments, the disclosed bioactive compositions and articles can be a preferred or most preferred composition or article and can comprise, consist of, or consist essentially of, the disclosed bioactive composition or article.

In embodiments, the disclosed methods of making and methods of using can be a preferred or most preferred method and can comprise, consist of, or consist essentially of, the disclosed methods.

In embodiments, the composition can have a high strength of from 200 MPa to 500 MPa, for example, from at least 200 MPa, at least 300 MPa, or at least 400 MPa, including intermediate values and ranges.

In embodiments, the composition can have a high fracture toughness of from 1.4 to 2.0 MPa·m$^{1/2}$, for example, from at least 1.4, 1.6, 1.8, or 2.0 MPa·m$^{1/2}$, including intermediate values and ranges.

In embodiments, the composition can have a combination of high strength of from 200 MPa to 500 MPa, and high fracture toughness of from 1.4 to 2.0 MPa·m$^{1/2}$.

Precursor Glass

In embodiments, the composition can be prepared from a precursor glass composition comprising a source of, for example:
  50 to 75 wt % $SiO_2$,
  1 to 5 wt % $Al_2O_3$,
  1 to 8 wt % $P_2O_5$,
  2 to 10 wt % CaO,
  5 to 20 wt % $Li_2O$,
  0.5 to 5 wt % $Na_2O$,
  0.5 to 8 wt % $ZrO_2$, and
  0.1 to 1.0 wt % $F^-$, based on a 100 wt % total of the composition.

In embodiments, the abovementioned precursor glass composition does not change significantly upon ceramming.

In embodiments, the disclosure provides a method of making the abovementioned glass-ceramic compositions comprising, for example:
  ceramming a precursor glass comprising a source of:
  50 to 75 wt % $SiO_2$,
  1 to 5 wt % $Al_2O_3$,
  1 to 8 wt % $P_2O_5$,
  2 to 10 wt % CaO.
  5 to 20 wt % $Li_2O$,
  0.5 to 5 wt % $Na_2O$,
  0.5 to 8 wt % $ZrO_2$, and
  0.1 to 1.0 wt % $F^-$, based on a 100 wt % total of the composition, by heating the glass at 650 to 750° C. for 0.5 to 10 hrs, and then heating at 750 to 850° C. for 0.5 to 20 hrs.

In embodiments, the method of making can further comprise, for example, ion exchanging the resulting glass-ceramic composition to create at least one compressive stress layer on at least one surface of the article to increase mechanical strength of the article.

Bioactive Composition

In embodiments, the disclosure provides a bioactive composition, comprising:
  a glass-ceramic comprised of:
    a first crystalline phase comprised of lithium disilicate; and
    a second crystalline phase selected from the group consisting of at least one of: wollastonite, fluoroapatite, cristobalite, β-quartz, lithiophosphate, or a combination thereof; and
  one or more live osteoblast cells, that is, a bioactive glass-ceramic including the disclosed composition and cells capable of synthesizing bone.

In embodiments, in the abovementioned bioactive composition the glass-ceramic composition can comprise, for example, a source of:
  50 to 75 wt % $SiO_2$,
  1 to 5 wt % $Al_2O_3$,
  1 to 8 wt % $P_2O_5$,
  2 to 10 wt % CaO.
  5 to 20 wt % $Li_2O$,
  0.5 to 5 wt % $Na_2O$,
  0.5 to 8 wt % $ZrO_2$, and
  0.1 to 1.0 wt % $F^-$, based on a 100 wt % total of the composition.

In embodiments, the glass-ceramic composition can comprise, for example, a source of:
  50 to 60 wt % $SiO_2$,
  1 to 3 wt % $Al_2O_3$,
  2 to 6 wt % $P_2O_5$,
  4 to 8 wt % CaO,
  7.5 to 12.5 wt % $Li_2O$,
  0.5 to 2 wt % $Na_2O$,
  1 to 4 wt % $ZrO_2$, and
  0.2 to 0.8 wt % $F^-$, based on a 100 wt % total of the composition.

In embodiments, the abovementioned bioactive composition can further comprise, for example, a source of 0.1 to 10 wt % $B_2O_3$, based on a 100 wt % total of the composition.

In embodiments, the disclosure provides a method of culturing osteoblast cells, i.e., a method of using the disclosed bioactive composition, comprising, for example:
  contacting the abovementioned bioactive composition with a suitable liquid medium.

In embodiments, the glass-ceramic composition of the bioactive composition can be combined or contacted with the suitable liquid medium prior to being contacted with the live osteoblast cell(s).

In embodiments, the contacting produces a proliferation of the osteoblast cells on the surface of the bioactive composition.

In embodiments, the contacting produces a proliferation of the osteoblast cells in the suitable liquid medium, such as the culture medium of MC3T3 cells: i.e., alpha-MEM supplemented with 10% fetal bovine serum and 1 mM sodium pyruvate.

In embodiments, the suitable liquid medium can include, for example, a simulated body fluid (SBF) composition. SBF is used for testing apatite formation activity of bioactive glasses/glass-ceramics. The disclosed bioactive glass-ceramics form in-situ a biologically active apatite layer (e.g., the mineral phase of bone and teeth) that can bond to bone and teeth, and can even bond to soft tissue. The potential applications of the disclosed bioactive glass-ceramics can include, for example, monolithic articles, composites, films, coating, or like forms, for use in repair of load-bearing bones, dental regeneration, treatment of dental hypersensitivity, artificial vertebrae, spinous spacers, intervertebral spacers, iliac spacers, granular fillers, scaffolds, middle-ear implant and in other types of small-bone replacement, wound healing, and like applications. The disclosed bioactive glass-ceramics are biocompatible with, for example, osteoblasts, keratinocytes, human umbilical vein endothelial cells (HUVEC), etc. (see for example, T. Kokubo et al., "How useful is SBF in predicting in vivo bone bioactivity?", Biomaterials, 27[15] 2907-15 (2006)).

In embodiments, the disclosed compositions and disclosed bioactive compositions can also have application in, for example: angiogenesis (HUVEC cells), wound healing (keratinocytes), bone tissue engineering (MC3T3 cells), and like applications.

In embodiments, the disclosed composition is biocompatible with various cell types in various applications, and are biologically active (i.e., bioactive).

In embodiments, the disclosed compositions and methods thereof are advantaged in several aspects, including for example:

glass-ceramic compositions having a combination of high strength and high toughness;

glass-ceramic compositions having excellent biocompatibility; and glass-ceramic compositions having a capability of supporting the growth and functionalization of osteoblastic cells.

In embodiments, the disclosed bioactive glass-ceramic compositions can further comprise, for example, a form factor selected from a hollow microsphere, a solid microsphere, or a combination thereof, that is, where the glass composition has a particle shape, such as a sphere, an elongated sphere or egg-shape, a rod, or like geometries. Table 1 lists representative examples of the disclosed compositions. The ceramming cycle for all examples 1 to 15 was 700° C. for 2 hr and 800° C. for 4 hr.

TABLE 1

Example compositions (Ex. 7 to 15) and control compositions (Ex. C-1 to C-6).

| Oxides (wt %) | C-1[1] | C-2 | C-3 | C-4 | C-5 | C-6 | 7 | 8 | 9 | 10 | 11 | 12 | 13 | 14 | 15 |
|---|---|---|---|---|---|---|---|---|---|---|---|---|---|---|---|
| $SiO_2$ | 70 | 65 | 60 | 55 | 60 | 60 | 70 | 65 | 60 | 55 | 60 | 60 | 60 | 60 | 60 |
| $B_2O_3$ | 0 | 0 | 0 | 0 | 0 | 0 | 0 | 0 | 0 | 0 | 0 | 0 | 2 | 4 | 6 |
| $Al_2O_3$ | 2.5 | 2.5 | 2.5 | 2.5 | 2.5 | 2.5 | 2.5 | 2.5 | 2.5 | 2.5 | 2.5 | 2.5 | 2.5 | 2.5 | 2.5 |
| $Li_2O$ | 12 | 12 | 12 | 12 | 15 | 12 | 12 | 12 | 12 | 12 | 15 | 12 | 12 | 12 | 12 |
| $Na_2O$ | 2 | 2 | 2 | 2 | 2 | 2 | 2 | 2 | 2 | 2 | 2 | 2 | 2 | 2 | 2 |
| CaO | 6 | 6 | 6 | 6 | 6 | 6 | 6 | 6 | 6 | 6 | 6 | 6 | 6 | 6 | 6 |
| $P_2O_5$ | 4 | 4 | 4 | 4 | 4 | 4 | 4 | 4 | 4 | 4 | 4 | 4 | 4 | 4 | 4 |
| $ZrO_2$ | 2 | 2 | 2 | 2 | 2 | 4 | 2 | 2 | 2 | 2 | 2 | 4 | 2 | 2 | 2 |
| $F^-$ | 0 | 0 | 0 | 0 | 0 | 0 | 0.5 | 0.5 | 0.5 | 0.5 | 0.5 | 0.5 | 0.5 | 0.5 | 0.5 |
| Phase assemblage[2] | A | A | A | B | C | D | E | E | F | G | G | H | F | F | F |
| Flexural strength (MPa) | — | — | — | — | — | — | 504 | 407 | 485 | 303 | — | — | — | — | — |
| Fracture toughness (MPa · $m^{1/2}$) | — | — | — | — | — | — | 1.8 | 1.9 | 2.2 | 2.2 | — | — | — | — | — |

[1] "C-#" designation represents a control example (i.e., C- to C-6).
[2] Phase assemblage key:
A = Lithium disilicate, cristobalite, wollastonite, β-quartz, lithiophosphate.
B = Lithium disilicate, wollastonite, lithiophosphate.
C = Lithium disilicate, lithium metasilicate, wollastonite, lithiophospahte.
D = Lithium disilicate, β-quartz, lithiophospahte.
E = Lithium disilicate, cristobalite, fluoroapatite, β-quartz.
F = Lithium disilicate, fluoroapatite, β-quartz, lithiophosphate.
G = Lithium disilicate, fluoroapatite, lithium metasilicate, β-quartz.
H = Lithium disilicate, fluoroapatite, β-quartz.
Sample Appearance: Samples of Examples 1 to 8 and 10 to 15 were translucent white; Example 9 was translucent/semi-transparent white.

In embodiments, the disclosed compositions can be free of (e.g., zero ppm or ppb), or substantially free of (e.g., trace amounts less than several ppm or ppb), at least one of, for example, $K_2O$, $K_2CO_3$, $Ca_3(PO_4)_2$, MgO, $TiO_2$, $As_2O_3$, $Sb_2O_3$, or combinations or mixtures thereof.

In embodiments, the disclosure provides precursor glass compositions that can be cerammed to produce glass-ceramics having excellent mechanical properties and biocompatibility. In embodiments, the disclosure provides glass-ceramics having high mechanical strength by forming an interlocking structure in the cerammed articles, which forces cracks to propagate along a tortuous path. Additionally, the presence of minor crystallite phases such as fluoroapatite and wollastonite in the disclosed compositions is beneficial to the growth, proliferation, and function of osteoblastic cell lines.

In embodiments, the precursor glass or source glass can comprise, for example, 50 to 75 wt % $SiO_2$, 1 to 5 wt % $Al_2O_3$, 5 to 20 wt % $Li_2O$, 0.5 to 5 wt % $Na_2O$, 0.5 to 8 wt % $ZrO_2$, and 0.1 to 1.0 $F^-$ wt % (i.e., fluoride ion), based on a 100 wt % total of the composition. In embodiments, a more preferred precursor glass composition, can be, for example, 50 to 60 wt % $SiO_2$, 1.0 to 3.0 wt % $Al_2O_3$, 0.1 to 4.0 wt % $B_2O_3$, 7.5 to 12.5 wt % $Li_2O$, 0.5 to 2.0 wt % $Na_2O$, 1.0 to 4.0 wt % $ZrO_2$, and 0.2 to 0.8 wt % $F^-$ ion based on a 100 weight percentage total (see Table 1).

In embodiments, the precursor glasses can be cerammed into glass-ceramic articles having high crystallinity of, for example, 80% or more, such as 80 to 95%. The major crystallite phases are comprised of lithium disilicate. The minor crystallite phases can be comprised of, for example, fluoroapatite, wollastonite, cristobalite, β-quartz, lithiophosphate, or mixtures thereof depending on composition targeted.

Figure 1:
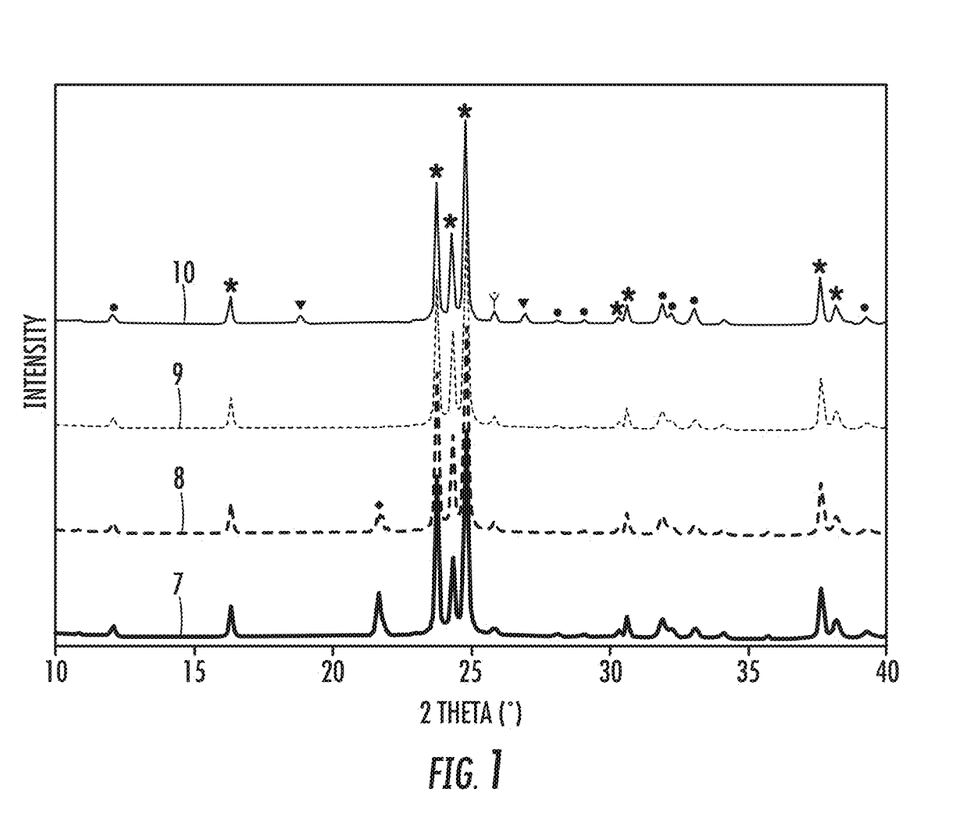
FIG. 1 shows X-ray diffraction spectra of example compositions 7 to 10. All specimens were cerammed using a cycle of 700° C. for 2 hr and then 800° C. for 4 hr.
Figure 2A:
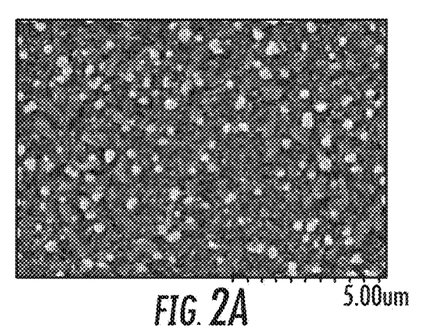
FIGS. 2A to 2D show SEM images of polished surfaces in example compositions 7 to 10 corresponding to FIGS. 2A, 2B, 2C, and 2D, respectively.
Figure 2B:
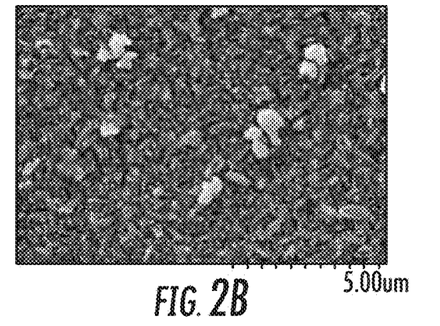
Figure 2C:
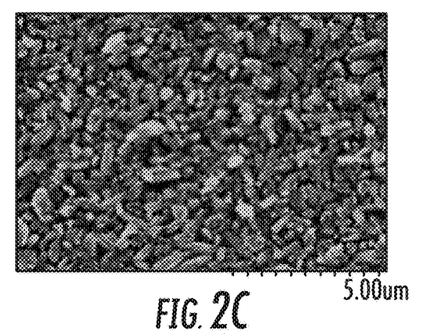
Figure 2D:
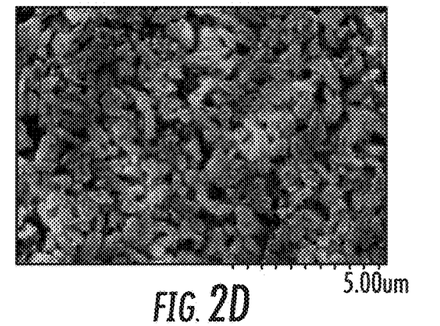
Figure 3A:
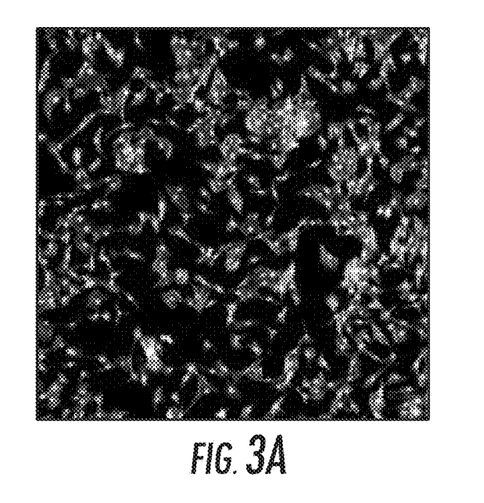
FIGS. 3A to 3D show confocal SEM images of MC3T3 cell growth in disclosed compositions 7 to 10 corresponding to FIGS. 3A, 3B, 3C, and 3D, respectively.
Figure 3B:
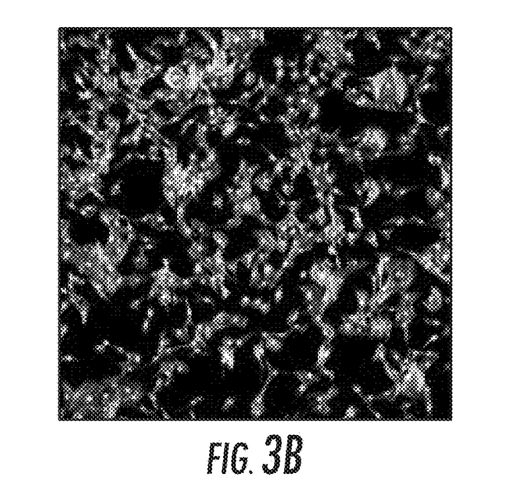
Figure 3C:
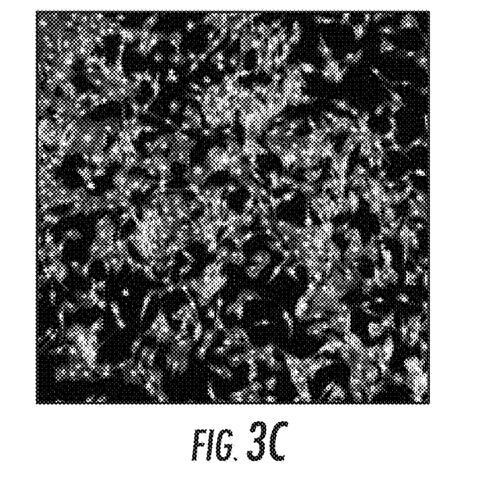
Figure 3D:
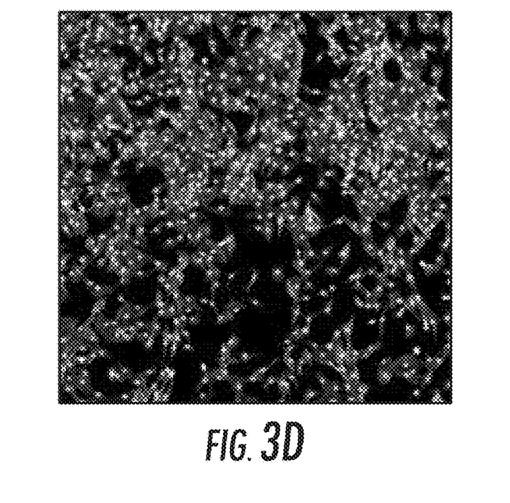

Referring to the Figures, FIG. 1 shows X-ray diffraction spectra of example compositions 7 to 10, where the reference numerals 7, 8, 9, and 10, correspond to example compositions 7 to 10, respectively, in Table 1. The significant peaks are identified (with marker shapes) as: lithium disilicate (asterisk), lithium metasilicate (triangle), fluoroapatite (dot), beta-quartz (square), and cristobalite (diamond). All specimens were cerammed using a cycle of 700° C. for 2 hr and then 800° C. for 4 hr.

In embodiments, the disclosed glass-ceramic articles composed of interlocking lithium disilicate can be easily obtained by ceramming precursor glasses at temperatures of from 700 to 900° C. for a period of time. A grain size of the lithium disilicate phase can be larger than 1 micrometer having a high aspect ratio that is typically formed in glassceramics. FIGS. 2A to 2D show SEM images of polished surfaces in example compositions 7 to 10 corresponding to FIGS. 2A, 2B, 2C, and 2D, respectively. All specimens were cerammed using a cycle of 700° C. for 2 hr and then 800° C. for 4 hr. Specimens were etched in 1% HF for one min prior to observation.

Although not bound by theory, it is believed that the presence of interlocking crystals can be a significant factor in developing toughening mechanisms including, for example, crack deflection and tortuous crack path, which mechanisms can contribute to the observed high fracture toughness and high flexural strength (Table 1). For example, a fracture toughness of over $1.5$ MPa·m$^{1/2}$ and a flexural strength of over 300 MPa can be achieved in selected glass-ceramic compositions.

In embodiments, the disclosed glass-ceramic product or residual glass can be ion exchanged to create a compressive stress layer in the surface of a ware to further improve mechanical strength.

In embodiments, excellent biocompatibility was demonstrated in the disclosed glass-ceramic compositions. Cell attachment was clearly observed through confocal images on the surfaces of compositions 7 to 9. MC 3T3 cells were cultured one day, fixed with 4% formaldehyde, and then stained with Alexa Fluor 568 phalloidin and DAPI prior to the confocal imaging. FIGS. 3A to 3D show confocal SEM images of MC3T3 cell growth in the disclosed compositions 7 to 10 corresponding to FIGS. 3A, 3B, 3C, and 3D, respectively. All specimens were cerammed using a cycle of 700° C. for 2 hr and then 800° C. for 4 hr. Cells were cultured one day, fixed with 4% formaldehyde, and then stained with Alexa Fluor 568 phalloidin and DAPI prior to the confocal imaging.

The ability of the disclosed glass-ceramics of examples compositions 7 to 10 to support cell proliferation was demonstrated by the expression of DNA from the cultured cells for absolute levels (FIG. 5A) and for relative levels (FIG. 5B) with respect to a TCT control. MCT3 cells were cultured on glass-ceramic discs. On day 4 and day 7, cells were digested with the digestion buffer (125 microgm/mL papain, 2 mM L-cysteine, 2 mMM EDTA) at 65° C. for overnight, the dsDNA amount was measured using Quant-iT™ PicoGreen® dsDNA Kit (Thermo Fisher). The increase of DNA concentration with increasing culture time provided additional evidence of the excellent biocompatibility of the disclosed compositions.

In embodiments, the disclosed glass-ceramics can be manufactured using a thin rolling, a float, a casting process, and like methods; and scaffolds can be produced using, for example, rapid prototyping, polymer foam replication, particle sintering, and like methods. Glass-ceramics of desired forms can be used to support cell growth and hard tissue regeneration.

In embodiments, the realized mechanical strength, biocompatibility, and biodegradation of the disclosed compositions can be influenced by the glass compositions. In embodiments, the disclosed glass compositions can further include, for example: $SiO_2$ which serves as the primary glass-forming oxide for precursor glass and can function to stabilize the networking structure of glass and glass-ceramics. In embodiments, the concentration of $SiO_2$ should be sufficiently high to form a lithium disilicate crystal phase when the precursor glass is heat treated to convert to a glass-ceramic (i.e., cerammed). However, the glasses can't contain too much $SiO_2$ since the melting temperature (200 poise temperature) of pure $SiO_2$ or high-$SiO_2$ glasses is undesirably high. In embodiments, glass or glass-ceramic compositions can comprise, for example, 68 to 82 wt % $SiO_2$, based on a 100 wt % total weight.

In embodiments, the $Al_2O_3$ may also provide stabilization to the networking structure. $Al_2O_3$ is favorable to the improvement of mechanical properties and chemical durability. However, too much $Al_2O_3$ generally increases the viscosity of the melt and decreases the fraction of lithium disilicate crystals to an extent that no interlocking structure can be formed. The $Al_2O_3$ concentration is preferably maintained in a reasonable range of, for example, from 1 to 5 wt %.

In embodiments, the addition of $B_2O_3$ can be beneficial to improved crack-resistance of the glass-ceramics, which is helpful for dental applications. Furthermore, a higher boron concentration can increase the degradation rate of the bioactive compositions, which property may be desired in applications such as bone regeneration.

$Li_2O$ is another significant component in the disclosed precursor glass compositions. $Li_2O$ is advantageous for forming lithium disilicate crystal phases. $Li_2O$ is called for to have at least 8 wt % $Li_2O$ to obtain glass-ceramics having lithium disilicate as a predominant phase. However, when the $Li_2O$ content gets too high, such as greater than 15 wt %, the precursor glasses become very fluid with low resistivity making it difficult to melt or form.

In embodiments, the disclosed glass and glass-ceramic compositions can include, for example, from 2 to 6 wt % $P_2O_5$, for example, as a nucleating agent to produce bulk nucleation. If the $P_2O_5$ concentration is too low, such as less than 2 wt %, the precursor glass does not crystallize. If the $P_2O_5$ concentration is too high, such as greater than 6 wt %, the denitrification upon cooling during precursor glass forming, can be difficult to control.

In embodiments, divalent cation oxides, such as alkaline earth oxides, can also be used to improve the melting behavior and the bioactivity of the glass. For example, CaO was found to combine with $P_2O_5$ to form apatite, or with $SiO_2$ to form wollastonite. Both apatite and wollastonite are known bioactive ceramics (see Hench, L. L., supra.).

In embodiments, including $Na_2O$ in the precursor glass in an amount of from 0.1 to 5 wt % can reduce the melting temperature of the precursor glass, and can shorten the ceramming cycle. Furthermore, including $Na_2O$ in the precursor glass can also increase the thermal expansion after ceramming if a higher thermal expansion (i.e., CTE) is desired in the glass-ceramic articles.

In embodiments, melting was accomplished at an elevated temperature, such as above 1300° C., to fuse the precursor glass materials. In embodiments, ceramming was the heat treatment of the melted glass that was used to crystallize the glass into a glass-ceramic material.

EXAMPLES

The following Examples demonstrate making, use, and analysis of the disclosed compositions and methods in accordance with the above general procedures.

Example 1

Preparation of Control Examples C-1 to C-6 and Actual Example Glass-Ceramic Compositions 7 to 15

Control and Actual Example Glass-Ceramic Compositions 1 to 15 listed in Table 1, and their respective glass source materials in the indicated amounts, including for example, silica, boric acid, alumina, lithium carbonate, sodium carbonate, limestone, spodumene, aluminum metaphosphate, were individually combined and melted in an electric furnace. Prior to melting, the precursor glass source materials were vigorously mixed in a plastic jar using a Turbula® mixer. Then the mixtures were transferred to a platinum crucible with an internal volume of approximately 650 cc and heated at 700° C. for 2 hr then 800° C. for 4 hr, and then the glass melt was poured on a steel plate, and annealed at 500° C.

Example 2

Preparation of Glass-Ceramic Discs

Glass-ceramic discs were prepared from cerammed parts. Precursor glass patties were cerammed in an electronic furnace using a cycle of 700° C. to 2 hr for nucleation and then 800° C. for 4 hr for crystal growth. After ceramming, the discs (12.5 mm in diameter×2.0 mm thick) were core-drilled using a diamond drill, and then ground and polished to a 1.0 micrometer finish using a $CeO_2$ slurry. All finished discs were cleaned by sonicating in an ultrasonic sonicator for 10 min.

Example 3

Method of Attachment and Growth of Bone Cells with the Bioactive Composition of Example 1

Glass-ceramic discs of Example 2 (made from compositions of the above working Example 1) were placed in wells of 24 well tissue culture treated microplates. Each composition has duplicate discs. MC 3T3 cells were then seeded (20K/2 mL) into the wells and some wells without any discs (Tissue Culture Treated (TCT) control). The microplates were cultured for 1, 4, or 7 days. Cells in the 1 day culture microplate were fixed with 4% formaldehyde, and then stained with Alexa Fluor 568 phalloidin and DAPI prior to the confocal imaging.

Figure 4A:
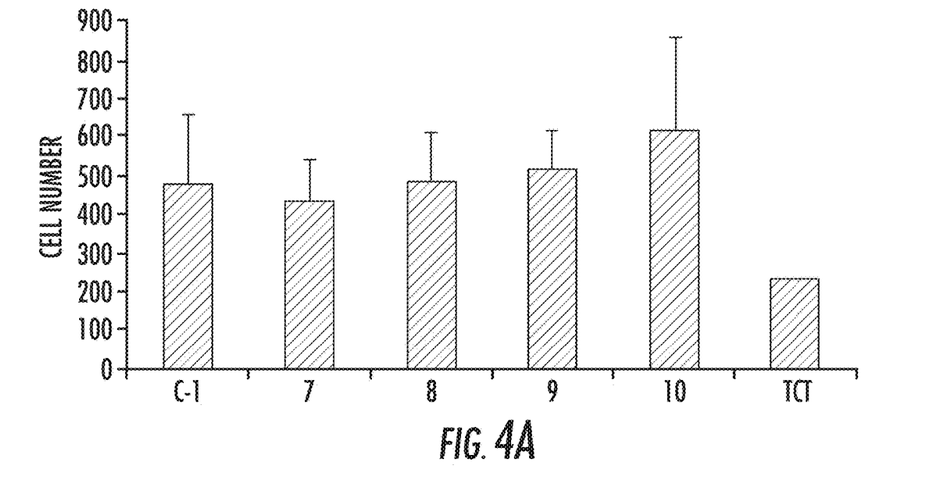
FIGS. 4A and 4B show Day 1 attachment and proliferation of MC3T3 cells on disclosed bioactive glass-ceramic discs: absolute level (absolute cell number; 4A) and relative levels with respect to an in vitro control: a Tissue Culture Treated® (TCT) well (relative cell number; 4B).
Figure 4B:
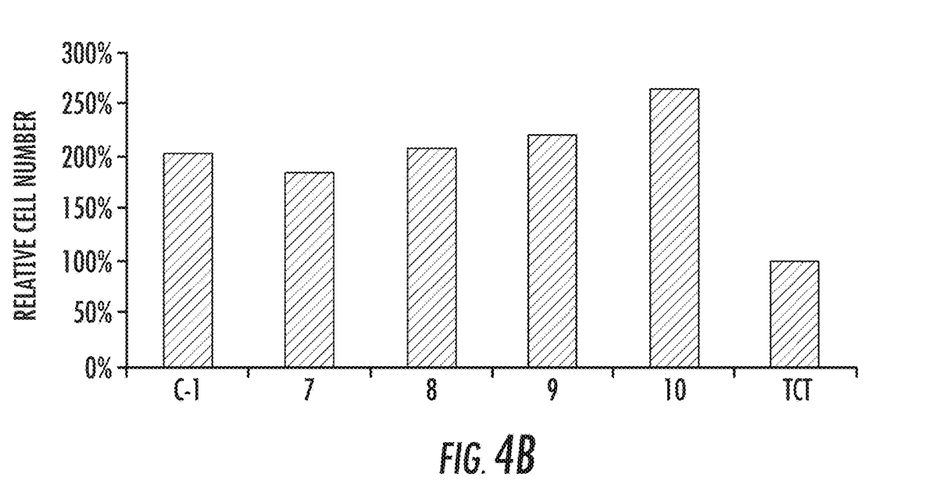

FIGS. 4A and 4B show Day 1 attachment and proliferation of MC3T3 cells on disclosed bioactive glass-ceramic discs of Example compositions 7, 8, 9, and 19 (see Table 1) with respect to a reference bioactive glass control compositions 1 (C-1) and an in vitro control: a Tissue Culture Treated® (TCT) well: absolute level (absolute cell number; 4A) and relative levels (relative cell number; 4B).

Figure 5A:
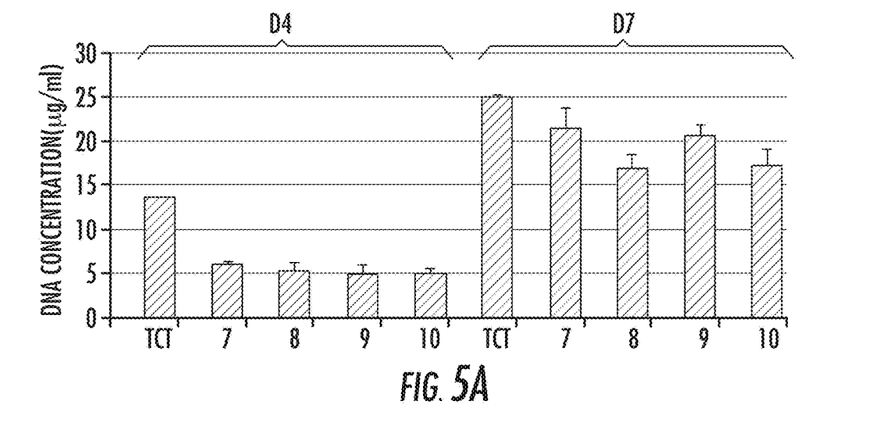
FIGS. 5A and 5B show cell proliferation results for disclosed compositions 7 to 10.
Figure 5B:
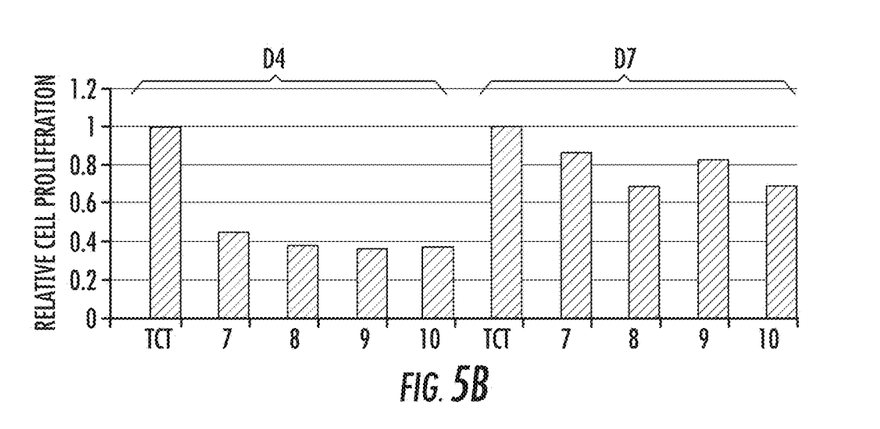

FIGS. 5A and 5B show cell proliferation results for disclosed compositions 7 to 10. Cells in the day 4 (D4) and day 7 (D7) culture plates were digested with the digestion buffer (125 microg/mL papain, 2 mM L-cysteine, 2 mM EDTA) at 65° C. for 16 hrs, the dsDNA amount was measured using Quant-iT™ PicoGreen® dsDNA Kit (Thermo Fisher). The increase of DNA concentration with increasing culture time provides additional evidence of their excellent biocompatibility.

MC3T3 cells were digested with papain and the amount of DNA was measured using a PicoGreen assay. D4 or D7 refers to Day 4 or Day 7 (as in "the $4^{th}$ day or $7^{th}$ day of cell culture"). TCT refers to a tissue culture treated microplate substrate available from Corning, Inc®. Glass-ceramic discs were placed in wells of 24 well tissue culture treated microplates. Each composition has duplicate discs. MC 3T3 cells were then seeded (20K/2 mL) into the wells and some wells without any discs (TCT control). The microplates were cultured for 4 or 7 days. On the day 4 and day 7, cells were digested with a digestion buffer (D-PBS containing 125 microg/mL papain, 2 mM L-cysteine, 2 mMM EDTA) at 65° C. in humid environment with shaking (60 rpm) for 16 hrs. An attempt was made to remove the lysed DNA from glass-ceramic discs by pipetting digestion solution up and down on the discs. The collected digestion solution was briefly centrifuged to remove any remaining particles. The dsDNA amount in the supernatant was measured using Quant-iT™ PicoGreen® dsDNA Kit (Thermo Fisher) according to the manufacturer's instruction.

Materials:

MC3T3E1 Subclone 14 (ATCC® CRL2594™)(see atcc.org/products/all/CRL-2594.aspx).

Quant-iT™ PicoGreen® dsDNA Kit (Invitrogen, #P11496). This kit contains Quant-iT™ PicoGreen® dsDNA Reagent (10 vials, each containing 100 microL aliquots), 25 mL of 20× TE buffer, 1 mL of 100 microg/mL Lambda DNA (dsDNA standard), Papain (Sigma-Aldrich, #P4762-25MG), L-cysteine (Sigma-Aldrich, #C1276-10G), EDTA (Sigma-Aldrich, #E6511), D-PBS (Thermo Fisher, #14190), a shaker set to 65° C., and a plate reader.

The disclosure has been described with reference to various specific embodiments and techniques. However, it should be understood that many variations and modifications are possible while remaining within the scope of the disclosure.

What is claimed is:

1. A bioactive composition, comprising:
 a glass-ceramic composition comprising
  a first crystalline phase comprising lithium disilicate, and
  a second crystalline phase that is apatite, wollastonite, fluorapatite, cristobalite, β-quartz, lithiophosphate, or a combination thereof; and
 at least one live osteoblast cell,
 wherein contacting the bioactive composition with a liquid medium produces proliferation of the osteoblast cell on a surface of the bioactive composition, and
 wherein the glass-ceramic composition comprises a source of:
  50 to 75 wt % $SiO_2$,
  1 to 5 wt % $Al_2O_3$,
  1 to 8 wt % $P_2O_5$,
  2 to 10 wt % $CaO$,
  5 to 20 wt % $Li_2O$,
  0.5 to 5 wt % $Na_2O$,
  0.5 to 8 wt % $ZrO_2$,
  0.1 to 10 wt % $B_2O_3$, and
  0.1 to 1.0 wt % $F^-$, based on a 100 wt % total of the composition.

2. The bioactive composition of claim 1, wherein the glass-ceramic composition comprises a source of:
  50 to 60 wt % $SiO_2$,
  1 to 3 wt % $Al_2O_3$,
  2 to 6 wt % $P_2O_5$,
  4 to 8 wt % $CaO$,
  7.5 to 12.5 wt % $Li_2O$,
  0.5 to 2 wt % $Na_2O$,
  1 to 4 wt % $ZrO_2$,
  0.1 to 10 wt % $B_2O_3$, and
  0.2 to 0.8 wt % $F^-$, based on a 100 wt % total of the composition.

3. The bioactive composition of claim 1, further comprising at least one compressive stress layer on the surface of the bioactive composition.

4. The bioactive composition of claim 1, further comprising a strength of from 200 MPa to 500 MPa.

5. The bioactive composition of any claim 1, further comprising a fracture toughness of from 1.4 to 2.0 $MPa·m^{1/2}$.

6. A bioactive composition, comprising:
a glass-ceramic composition comprising
a first crystalline phase comprising lithium disilicate, and
a second crystalline phase comprising wollastonite, cristobalite, β-quartz, lithiophosphate, or a combination thereof; and
at least one live osteoblast cell;
wherein contacting the bioactive composition with a liquid medium produces proliferation of the osteoblast cell on a surface of the bioactive composition, and
wherein the glass-ceramic composition comprises a source of:
50 to 75 wt % $SiO_2$,
1 to 5 wt % $Al_2O_3$,
1 to 8 wt % $P_2O_5$,
2 to 10 wt % CaO,
5 to 20 wt % $Li_2O$,
0.5 to 5 wt % $Na_2O$,
0.5 to 8 wt % $ZrO_2$,
0.1 to 10 wt % $B_2O_3$, and
0.1 to 1.0 wt % $F^-$, based on a 100 wt % total of the composition.

7. The bioactive composition of claim 6, wherein the glass-ceramic composition comprises a source of:
50 to 60 wt % $SiO_2$,
1 to 3 wt % $Al_2O_3$,
2 to 6 wt % $P_2O_5$,
4 to 8 wt % CaO,
7.5 to 12.5 wt % $Li_2O$,
0.5 to 2 wt % $Na_2O$,
1 to 4 wt % $ZrO_2$,
0.1 to 10 wt % $B_2O_3$, and
0.2 to 0.8 wt % $F^-$, based on a 100 wt % total of the composition.

8. The bioactive composition of claim 6, further comprising at least one compressive stress layer on the surface of the bioactive composition.

9. The bioactive composition of claim 6, further comprising a strength of from 200 MPa to 500 MPa.

10. The bioactive composition of any claim 6, further comprising a fracture toughness of from 1.4 to 2.0 $MPa \cdot m^{1/2}$.

11. A method of culturing osteoblast cells, comprising:
contacting the bioactive composition of claim 1 with the liquid medium to produce a proliferation of the at least one osteoblast cell on the first crystalline phase and on the second crystalline phase.

12. The method of claim 11, wherein contacting with the liquid medium produces a proliferation of the at least one osteoblast cell in the liquid medium.

13. The method of claim 12, wherein the liquid medium comprises a simulated body fluid composition.

14. A method of culturing osteoblast cells, comprising:
contacting the bioactive composition of claim 6 with the liquid medium to produce a proliferation of the at least one osteoblast cell on the first crystalline phase and on the second crystalline phase.

* * * * *

UNITED STATES PATENT AND TRADEMARK OFFICE
CERTIFICATE OF CORRECTION

PATENT NO. : 11,814,649 B2
APPLICATION NO. : 16/163013
DATED : November 14, 2023
INVENTOR(S) : Huayun Deng et al.

It is certified that error appears in the above-identified patent and that said Letters Patent is hereby corrected as shown below:

On the Title Page

On page 3, in Column 1, item (56) under "Other Publications", Line 4, delete "stronium" and insert -- strontium --.

On page 3, in Column 2, item (56) under "Other Publications", Line 10, delete "SiO2Na20." and insert -- SiO2.Na2O. --.

On page 3, in Column 2, item (56) under "Other Publications", Line 33, delete "(2003." and insert -- (2003). --.

On page 3, in Column 2, item (56) under "Other Publications", Line 36, delete "Detinal" and insert -- Dentin --.

On page 3, in Column 2, item (56) under "Other Publications", Line 40, delete "Microplasitcs" and insert -- Microplastics --.

On page 3, in Column 2, item (56) under "Other Publications", Line 41, delete "12251228 (2009" and insert -- 1225-1228 (2009) --.

On page 3, in Column 2, item (56) under "Other Publications", Line 53, delete "Manetization" and insert -- Magnetization --.

On page 3, in Column 2, item (56) under "Other Publications", Line 55, delete "Ehg" and insert -- Eng --.

On page 4, in Column 1, item (56) under "Other Publications", Line 11, delete "Monoflurophosphate" and insert -- Monofluorophosphate --.

On page 4, in Column 1, item (56) under "Other Publications", Line 19, delete "Propmotes" and insert Signed and Sealed this
Fourteenth Day of May, 2024

Katherine Kelly Vidal
*Director of the United States Patent and Trademark Office*

CERTIFICATE OF CORRECTION (continued)
U.S. Pat. No. 11,814,649 B2

-- Promotes --.

On page 4, in Column 1, item (56) under "Other Publications", Lines 33-34, delete "SI02-NA20-FE203-CA0-P205_B203" and insert -- SiO2-NA2O-FE2O3-CAO-P2O5-B2O3 --.

On page 4, in Column 1, item (56) under "Other Publications", Line 52, delete "Bioactivty" and insert -- Bioactivity --.

On page 4, in Column 1, item (56) under "Other Publications", Line 52, delete "Mechnical" and insert -- Mechanical --.

On page 4, in Column 1, item (56) under "Other Publications", Line 54, delete "Biomoleclar" and insert -- Biomolecular --.

On page 4, in Column 1, item (56) under "Other Publications", Line 56, delete "Additiona" and insert -- Addition --.

On page 4, in Column 1, item (56) under "Other Publications", Line 66, delete "Solid;" and insert -- Solids; --.

On page 4, in Column 1, item (56) under "Other Publications", Line 66, delete "287-391." and insert -- 387-391. --.

On page 4, in Column 2, item (56) under "Other Publications", Line 3, delete "(Year:2014." and insert -- (Year:2014). --.

On page 4, in Column 2, item (56) under "Other Publications", Line 8, delete "Febuary" and insert -- February --.

On page 4, in Column 2, item (56) under "Other Publications", Line 43, delete "baed" and insert -- based --.

On page 4, in Column 2, item (56) under "Other Publications", Line 44, delete "Sciemce:" and insert -- Science: --.

On page 5, in Column 1, item (56) under "Other Publications", Line 23, delete "Mechanism," and insert -- Mechanisms", --.

On page 5, in Column 2, item (56) under "Other Publications", Line 2, delete "aspromising" and insert -- as promising --.

On page 5, in Column 2, item (56) under "Other Publications", Line 8, delete "B203-Si02-P205-Na20-CaO" and insert -- B2O3-SiO2-P2O5-Na2O-CaO --.

On page 5, in Column 2, item (56) under "Other Publications", Lines 12-13, delete "Si02.Na20.CaO.K 20.Mg O.P205" and insert -- SiO2.Na2O.CaO.K2O.MgO.P2O5 --.

CERTIFICATE OF CORRECTION (continued)
U.S. Pat. No. 11,814,649 B2

On page 5, in Column 2, item (56) under "Other Publications", Line 13, delete "Al203 and B203" and insert -- Al2O3 and B2O3 --.

On page 5, in Column 2, item (56) under "Other Publications", Line 16, delete "inomercementa"," and insert -- ionomer cement", --.

In the Claims

In Column 12, Line 65, in Claim 5, delete "of any claim" and insert -- of claim --.

In Column 13, Line 8, in Claim 6, delete "cell;" and insert -- cell, --.

In Column 14, Line 11, in Claim 10, delete "of any claim" and insert -- of claim --.